United States Patent [19]
Durette et al.

[11] Patent Number: 5,658,922
[45] Date of Patent: Aug. 19, 1997

[54] 4-AZA-PREGNANE 5α-REDUCTASE ISOZYME 1 INHIBITORS

[75] Inventors: Philippe L. Durette, New Providence; Soumya P. Sahoo, Old Bridge, both of N.J.

[73] Assignee: Merck & Co., Inc., Rahway, N.J.

[21] Appl. No.: 537,876

[22] PCT Filed: Jun. 27, 1994

[86] PCT No.: PCT/US94/07220

§ 371 Date: Oct. 31, 1995

§ 102(e) Date: Oct. 31, 1995

[87] PCT Pub. No.: WO95/00147

PCT Pub. Date: Jan. 5, 1995

Related U.S. Application Data

[63] Continuation-in-part of Ser. No. 83,798, Jun. 28, 1993, abandoned.

[51] Int. Cl.[6] .......................... C07D 221/18; A61K 31/44
[52] U.S. Cl. ................................. 514/284; 546/77
[58] Field of Search .......................... 514/284; 546/77

[56] References Cited

U.S. PATENT DOCUMENTS

| | | |
|---|---|---|
| 2,227,876 | 1/1941 | Bolt et al. . |
| 3,239,417 | 3/1966 | Di Tullio . |
| 3,264,301 | 8/1966 | Doorenbos et al. . |
| 3,285,918 | 11/1966 | Doorenbos et al. . |
| 4,220,775 | 9/1980 | Rasmusson et al. . |
| 4,317,817 | 3/1982 | Blohm et al. . |
| 4,377,584 | 3/1983 | Rasmusson et al. . |
| 4,596,812 | 6/1986 | Chidsey, III et al. . |
| 4,732,897 | 3/1988 | Cainelli et al. . |
| 4,760,071 | 7/1988 | Rasmusson et al. . |
| 4,845,104 | 7/1989 | Carlin et al. . |
| 4,859,681 | 8/1989 | Rasmusson et al. . |
| 4,882,319 | 11/1989 | Holt et al. . |
| 4,888,336 | 12/1989 | Holt et al. . |
| 4,910,226 | 3/1990 | Holt et al. . |
| 5,049,562 | 9/1991 | Rasmusson et al. ............ 514/284 |
| 5,098,908 | 3/1992 | Steinberg et al. ............ 514/284 |
| 5,116,983 | 5/1992 | Bhattacharya et al. ............ 514/284 |
| 5,237,064 | 8/1993 | Bakshi et al. ............ 514/284 |
| 5,278,159 | 1/1994 | Bakshi et al. ............ 514/284 |
| 5,512,555 | 4/1996 | Waldstreicher ............ 514/284 |
| 5,543,417 | 8/1996 | Waldstreicher ............ 514/284 |
| 5,567,708 | 10/1996 | Rasmusson et al. ............ 514/284 |
| 5,571,817 | 11/1996 | Rasmusson et al. ............ 514/284 |
| 5,578,599 | 11/1996 | Diani et al. ............ 514/284 |

FOREIGN PATENT DOCUMENTS

| | | |
|---|---|---|
| 970962 | 7/1975 | Canada . |
| 0004949 | 10/1979 | European Pat. Off. . |
| 0155096 | 9/1985 | European Pat. Off. . |
| 0200859 | 11/1986 | European Pat. Off. . |
| 0277002 | 6/1988 | European Pat. Off. . |
| 0289327 | 11/1988 | European Pat. Off. . |
| 0314199 | 5/1989 | European Pat. Off. . |
| 0343954 | 11/1989 | European Pat. Off. . |
| 0375344 | 6/1990 | European Pat. Off. . |
| 0375345 | 6/1990 | European Pat. Off. . |
| 0375347 | 6/1990 | European Pat. Off. . |
| 0375349 | 6/1990 | European Pat. Off. . |
| 0 572 166 | 12/1993 | European Pat. Off. . |
| 1465544 | 11/1965 | France . |
| WO 91/12261 | 8/1991 | WIPO . |
| WO 93/23039 | 11/1993 | WIPO . |

OTHER PUBLICATIONS

The Daily (Tuesday, May 7, 1996), "New Data on Proscar, Abbott's Hytrin Show Conflicting Results".

Wall Street Journal (Tuesday, May 7, 1996), "Study Finds Abbott's Prostate Drug is Much More Effective than Merck's", p. B4.

US News & World Report, May 20, 1996, "Zapping a problem prostate".

Neri et al., Endo., vol. 91, No. 2, pp. 427–437 (1972), "A biological profile of a nonsteroidal antiandrogen, SCH 13521 ...".

Nayfeh et al., Steroids, vol. 14, pp. 269–283 (1969), "Metabolism of progesterone by rat testicular homogenates".

Voight et al., Endo., vol. 92, No. 4, pp. 1216–1222, "The antiandrogenic action of 4–androsten–3–one–17beta–carboxylic acid ...".

Doorenbos et al., J. Pharm. Sci., vol. 62, No. 4, pp. 638–640 (1973), "Synthesis and antimicrobial properties of 17beta–isopentyloxy–4–aza–5alpha–androstane and the 4–methyl derivative".

Doorenbos et al., J. Pharm. Sci., vol. 60, No. 8, pp. 1234–1235 (1971), "4,17alpha–Dimethyl–4–aza–5alpha–androstan–17 beta–ol acetate and related azasteroids".

Doorenbos et al., J. Pharm. Sci., vol. 63, No. 4, pp. 620–622 (1974), "Synthesis and evaluation of antimicrobial properties of amidinoazaandrostanes and guanidinoazaandrostanes".

(List continued on next page.)

*Primary Examiner*—Donald G. Daus
*Attorney, Agent, or Firm*—Catherine D. Fitch; Melvin Winokur

[57] ABSTRACT

Compounds of formula (I), wherein: $R^1$ is selected from the group consisting of hydrogen and methyl; $R^2$ is selected from the group consisting of methyl and ethyl; $R^3$ is selected from the group consisting of hydrogen and methyl; and the C1–C2 carbon-carbon bond may be a single or double bond. Such compounds are useful in the treatment of pathologic conditions that benefit from blockade of isozymes of 5α-reductase.

5 Claims, No Drawings

OTHER PUBLICATIONS

Rasmusson et al., J. Med. Chem., vol. 29, No. 11, pp. 2298–2315 (1986), "Azasteroids: Structure–activity relationships for Inhibition of 5alpha–reductase . . . ".

Brooks et al., The Prostate, vol. 9, No. 1, pp. 65–75 (1986), "Prostatic effects induced in dogs by chronic or acute oral administration . . . ".

Brooks et al., Steroids, vol. 47, No. 1, pp. 1–19 (1986), "5alpha–reductase inhibitory and anti–androgenic activities of some 4–azasteroids in the rat".

Liang et al., Endo., vol. 117, No. 2, pp. 571–579 (1985), "Species differences in prostatic steroid 5alpha–reductase of rat, dog, and human".

Rasmusson et al., J. Med. Chem., vol. 27, No. 12, pp. 1690–1701 (1984), "Azasteroids as inhibitors of rat prostatic 5alpha–reductase".

Back et al., J. Org. Chem., vol. 54, No. 8, pp. 1904–1908 (1989), "N–Chloroazasteroids: A novel class of reactive steroid analogues . . . ".

Liang et al., Chem. Abstracts, vol. 95, 109055i, "Inhibition of 5alpha–reductase, receptor binding, and nuclear uptake of androgens in the prostate . . . ".

Kadohama et al., JNCI, vol. 74, No. 2, pp. 475–481 (1985), "Retardation of prostate tumor progression in the noble rat . . . ".

Andriole et al., The Prostate, vol. 10, pp. 189–197 (1987), "The effect of 4MA, a potent inhibitor of 5alpha–reductase, on the growth of androgen–responsive human genitourinary tumors . . . ".

Bingham et al., J. Endocr., vol. 57, pp. 111–121 (1973), "The metabolism of testosterone by human male scalp skin".

Kedderis et al., Toxicol. Appl. Pharmacol., vol. 103, pp. 222–227 (1990), "Studies with nitrogen–containing steroids and freshly isolated rat hepatocytes . . . ".

Metcalf et al., Bioorganic Chemistry, vol. 17, pp. 372–376 (1989), "Potent inhibition of human steroid 5alpha–reductase . . . ".

Levy et al., Biochemistry, vol. 29, pp. 2815–2824 (1990), "Inhibition of rat liver steroid 5alpha–reductase by 3–androstene–3–carboxylic acids . . . ".

Holt et al., J. Med. Chem., vol. 33, No. 3, pp. 943–950 (1990), "Inhibition of steroid 5alpha–reductase by unsaturated 3–carboxysteroids".

Levy et al., J. Steroid Biochem., vol. 34, Nos. 1–6, pp. 571–575 (1989), "Interaction between rat prostatic steroid 5alpha–reductase and 3–carboxy–17beta–substituted steroids: . . . ".

Holt et al., J. Med. Chem., vol. 33, No. 3, pp. 937–942 (1990), "Steroidal A ring aryl carboxylic acids . . . ".

Metcalf et al., TIPS, vol. 10, pp. 491–495 (1985), "Inhibitors of steroid 5alpha–reductase in benign prostatic hyperplasia, male pattern baldness and acne".

Murphy et al., Steroids, vol. 35, No. 3, pp. 1–7 (1980), "The effect of estradiol on a 25–hydroxycholecalciferol binding protein in the uterus of the mouse".

Stone et al., The Prostate, vol. 9, pp. 311–318 (1986), "Estrogen formation in human prostatic tissue from patients with and without benign prostatic hyperplasia".

Labrie et al., The Lancet, No. 1986, No. 8515, pp. 1095–1096, "Combination therapy in prostate cancer".

Rittmaster et al., J. Clin. Endocrin. and Metab., vol. 55, No. 1, pp. 188–193 (1987), "The effects of N,N–diethyl–4–methyl–3–oxo–4–aza–5alpha–androstane–17beta–carboxamide . . . ".

Diani et al., J. Clin. Endocrin. and Metab., vol. 74, No. 2, pp. 345–350 (1990), "Hair growth effects of oral administration of finasteride, a steroid 5alpha–reductase inhibitor, . . . ".

Bruchovsky et al., J. Clin. Endocrinol. and Metab., vol. 67, No. 4, pp. 806–816 (1988), "Kinetic parameters of 5alpha–reductase activity in stroma and epithellium of normal, . . . ".

Hudson, J. Steroids Biochem., vol. 26, pp. 349–353 (1987), "Comparison of nuclear 5alpha–reductase activities in the stromal and epithelial fractions of human prostatic tissue".

Moore et al., J. Biol. Chem., vol. 251, No. 19, pp. 5895–5900 (1976), "Steroid 5alpha–reductase in cultured human fibroblasts".

Andersson et al., J. Biol. Chem., vol. 264, No. 27, pp. 16249–16255 (1989), "Expression cloning and regulation of steroid 5alpha–reductase, and enzyme essential for male sexual . . . ".

Andersson et al., Proc. Nat'l Acad. Science, vol. 87, pp. 3640–3644 (1990), "Structural and biochemical properties of cloned and expressed human and rat steroid 5alpha–reductases".

Andersson et al., Nature, vol. 354, pp. 159–161 (1991), "Deletion of steroid 5alpha–reductase 2 gene in male pseudohermaphroditism".

Wilson, Biol. of Reproduct., vol. 46, pp. 168–173 (1992), "Syndromes of androgen resistance".

Geldof et al., Eur. J. Cancer, vol. 26, No. 2, p. 188 (1990), "Enzyme inhibitors in hormone dependent prostate cancer treatment".

Geldof et al., J. Cancer Res. Clin. Oncol., vol. 118, pp. 50–55 (1992), "Consideration of the use of 17beta–N, N–diethylcarbamoyl–4–methyl–4–aza–5–alpha–androstan–3–one . . . ".

Brooks et al., The Prostate, vol. 18, pp. 215–227 (1991), "Effect of castration, DES, flutamide, and the 5alpha–reductase inhibitor, MK–906, on the growth of the dunning rat . . . ".

Masubuchi et al., Eur. J. Pharm., vol. 183, No. 5, p. 1757 (1990), "Lack of dihydrotestosterone inhibition and induction of androstenedione were found in . . . ".

Harris et al., Proc. Nat'l Acad. Sci., vol. 89, pp. 10787–10789 (1992), "Identification and selective inhibition of an isozyme of steroid 5alpha–reductase in human scalp".

Mellin et al., J. Steroid Biochem. Molec. Biol., vol. 44, pp. 121–131 (1993), "Azasteroids as inhibitors of testosterone 5alpha–reductase in mammalian skin".

Stinson, Chem. Eng. News, pp. 7–8 (Jun. 29, 1992), "Prostate drug Proscar cleared for marketing".

Helliker, Wall St. Journal, A1 and A7 (Jun. 7, 1991), "Alopecia sufferers seek to suffer less, and not in silence".

Burger, Medicinal Chemistry, (2nd ed., 1960), p. 42, "Reactivity and intensity of action . . . ".

4-AZA-PREGNANE 5α-REDUCTASE ISOZYME 1 INHIBITORS

CROSS REFERENCE TO RELATED APPLICATIONS

The present application is a national phase application under 35 U.S.C. §371 of PCT application Ser. No. PCT/US94/07220, filed Jun. 27, 1994, which, in turn, is a continuation in part of U.S. Ser. No. 08/083,798 filed Jun. 28, 1993, presently abandoned.

FIELD OF THE INVENTION

The present invention provides novel compounds, novel compositions, methods of their use and methods of their manufacture, where such compounds are generally pharmacologically useful as agents in therapies whose mechanism of action rely on the selective inhibition of the isozyme 5α-reductase 1.

BACKGROUND OF THE INVENTION

Certain undesirable physiological manifestations, such as acne vulgaris, seborrhea, female hirsutism, male pattern baldness (alopecia) and benign prostatic hyperplasia, are the result of hyperandrogenic stimulation caused by an excessive accumulation of testosterone or similar androgenic hormones in the metabolic system. Early attempts to provide a chemotherapeutic agent to counter the undesirable results of hyperandrogenicity resulted in the discovery of several steroidal antiandrogens having undesirable hormonal activities of their own. The estrogens, for example, not only counteract the effect of the androgens but have a feminizing effect as well. Non-steroidal antiandrogens have also been developed, for example, 4'-nitro-3'-trifluoromethyl-isobutyranilide. See Neri, et al., *Endocrinol.* 1972, 91 (2). However, these products, though devoid of hormonal effects, compete with all natural and androgens for receptor sites, and hence have a tendency to feminize a male host or the male fetus of a female host and/or initiate feed-back effects which would cause hyperstimulation of the testes.

The principal mediator of androgenic activity in some target organs, e.g. the prostate, is 5α-dihydrotestosterone, formed locally in the target organ by the action of testosterone-5α-reductase. Inhibitors of testosterone-5α-reductase will serve to prevent or lessen symptoms of hyperandrogenic stimulation in these organs. See especially U.S. Pat. No. 4,377,584 assigned to Merck & Co., Inc., issued Mar. 22, 1983. It is now known that a second 5α-reductase isozyme exists, which interacts with epidermal tissues, especially in scalp tissues. This form is conventionally designated as 5α-reductase 1, while the isozyme that principally interacts within the prostatic tissues is designated as 5α-reductase 2. Both isozymes are active in the prostatic tissues. In the treatment of hyperandrogenic disease conditions, e.g. benign prostatic hyperplasia (BPH), it would be desirable to have one drug entity which is active against both isozymes in the prostate to significantly inhibit dihydrotestosterone production, while also having another drug entity which is highly selective for inhibiting the isozyme 5α-reductase 1 associated with the scalp, for use in treating conditions of the skin and scalp, e.g. acne and alopecia in males and hirsutism in females. Additionally, such a selective 5α-reductase 1 inhibitor could also be used in combination with finasteride (PROSCAR®), which is highly selective for 5α-reductase 2, for therapy in the treatment of BPH. Therefore it is an object of this invention to provide compounds that have sufficient activity in the inhibition of 5α-reductase isozyme 1. It is an additional object of this invention to provide compounds that alone or in combination with inhibitors of 5α-reductase 2 are useful in the treatment and/or prevention of benign prostatic hyperplasia. It is an additional object of this invention to provide compounds that are useful in the treatment of female hirsutism, male pattern baldness, acne, androgenetic alopecia, prostatic cancer, and insufficient plasma levels of high density lipoproteins. The compounds of the invention have utility in one or more of the aforementioned areas.

SUMMARY OF THE INVENTION

The compounds of the present invention are those of the general structural formula I:

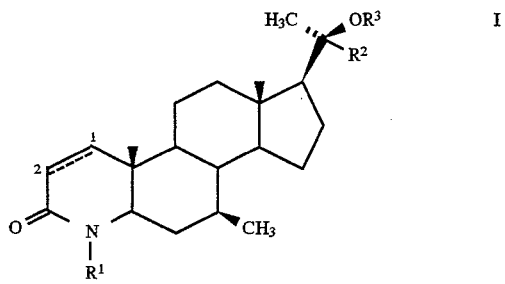

wherein:

$R^1$ is selected from the group consisting of hydrogen and methyl;

$R^2$ is selected from the group consisting of methyl and ethyl;

$R^3$ is selected from the group consisting of hydrogen and methyl; and the C1–C2 carbon-carbon bond may be a single or double bond.

DETAILED DESCRIPTION OF THE INVENTION

The term "pharmacologically effective amount" shall mean that amount of a drug or pharmaceutical agent that will elicit the biological or medical response of a tissue, system, animal or human that is being sought by a researcher or clinician.

The compounds of the present invention can be administered in such oral dosage forms as tablets, capsules (each including timed release and sustained release formulations), pills, powders, granules, elixirs, tinctures, suspensions, syrups and emulsions. Likewise, they may also be administered in intravenous (both bolus and infusion), intraperitoneal, subcutaneous, topical, or intramuscular form, all using forms well known to those of ordinary skill in the pharmaceutical arts. An effective but non-toxic amount of the compound desired can be employed as an antiandrogenic agent.

The compounds of the present invention can be prepared readily according to the following reaction Scheme and Examples or modifications thereof using readily available starting materials, reagents and conventional synthesis procedures. In these reactions, it is also possible to make use of variants which are themselves known to those of ordinary skill in this art, but are not mentioned in greater detail.

Synthesis Scheme

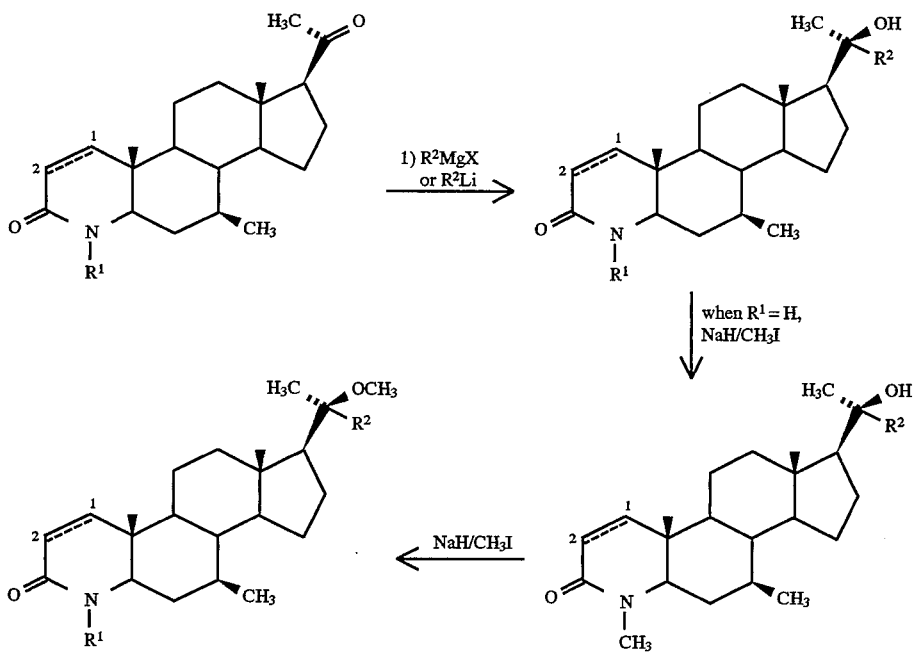

The most preferred compounds of the invention are any or all of those specifically set forth in these examples. These compounds are not, however, to be construed as forming the only genus that is considered as the invention, and any combination of the compounds or their moieties may itself form a genus. The following examples further illustrate details for the preparation of the compounds of the present invention. Those skilled in the art will readily understand that known variations of the conditions and processes of the following preparative procedures can be used to prepare these compounds. The procedures for the starting materials used in Examples 2–6, 7β-methyl-4-aza-5α-pregnan-3,20-dione and 7β-methyl-4-aza-5α-pregn-1-ene-3,20-dione, are analogous to those previously reported (U.S. Pat. No. 4,377,584 to Merck & Co., Inc. issued Mar. 22, 1983) and are collectively reported in Example 1. All temperatures are degrees Celsius unless noted otherwise.

EXAMPLE 1

3-Acetoxy-pregn-5-ene-20-ol

Sodium borohydride (21 gm) was added to a solution of pregnenolone acetate (100 g, 0.28 mol) in absolute ethanol (1 L) and methylene chloride (0.4 L) at –10° C. After stirring overnight at 4° C., another amount of sodium borohydride (10.5 gm) was added and the reaction stirred at room temperature overnight. The reaction mixture was quenched by pouring into 5% sodium phosphate monobasic (2 L) and extracted with methylene chloride. The organic extracts were dried over anhydrous magnesium sulfate and filtered through a pad of anhydrous sodium sulfate. The solvent was removed by rotoevaporation to give the title compound (97.6 gm, 87% yield).

3-Acetoxy-20-tert-butyldimethylsilyloxy-pregn-5-ene

Imidazole (203.7 gm, 2.28 mol) was added to a stirred suspension of 3-acetoxy-pregn-5-ene-20-ol (361 gm, 1 mol) in dimethylformamide (3.7 L). t-Butyldimethylsilyl chloride (228.9 mg, 1.52 mol) was added over a 10–15 min period. The mixture was stirred at room temperature for 3 days. The dimethylformamide was removed by decantation and methanol (50 mL) was added to it. Water (4 L) was added and the solution extracted with ethyl acetate (2×4 L). The precipitant remaining behind after decantation was dissolved in ethyl acetate and added to the above ethyl acetate extracts. The combined solvent extracts were washed with water, saturated salt solution, and dried over anhydrous magnesium sulfate. The solvent was removed by rotoevaporation and the product purified by column chromatography on silica gel eluted with 2:1 hexane-methylene chloride followed by 1:1 hexane-methylene chloride. The title compound was isolated as a mixture of 20α- and _β-isomers (363.3 gm, 76% yield).

3-Acetoxy-20-tert-butyldimethylsilyloxy-pregn-5-ene-7-one

To a solution of 3-acetoxy-20-tert-butyldimethylsilyloxy-pregn-5-ene (337 gm, 0.71 mol) in methyl ethyl ketone (4 L) was added N-hydroxyphthalimide (115.8 gm, 0.71 mol) and dibenzoyl peroxide (1.1 gm, 4.4 mmol). Air was bubbled through the reaction as the reaction was refluxed for 7.5 hr. Additional N-hydroxyphthalimide (9 gm) and dibenzoyl peroxide (0.1 gm) was added and reflux continued for 5 hr. The solvent was removed by rotoevaporation and methylene chloride (0.7 L) was added and warmed to 40° C. Upon cooling to room temperature, the suspension was filtered and the filtrate washed with methylene chloride (0.2 L). The filtrate was rotoevaporated and treated with pyridine (1.35 L) and acetic anhydride (135 mL). After stirring overnight, the solvent was removed by rotoevaporation and the dark orange oil dissolved in methanol (0.6 L). The mixture was heated to 50° C. and then cooled to room temperature. The solution was allowed to stand for 3 days and then cooled in an ice bath. The precipitant was filtered, washed with methanol, and dried to yield the title compound (110.6 gm, 32% yield). The filtrate was rotoevaporated to a dry gum to yield 253 gm of the crude product.

20-tert-Butyldimethylsilyloxy-7-methyl-pregn-5-ene-3,7-diol

A solution of 3-acetoxy-20-tert-butyldimethylsilyloxy-pregn-5-ene-7-one (279 gm, 0.57 mol) in tetrahydrofuran (5.6 L) was cooled to 4° C. A 3M solution of methyl magnesium chloride in tetrahydrofuran (1.037 L, 3.1 mol) was added at such a rate as to keep the temperature <0° C. The ice bath was removed and the reaction allowed to warm to room temperature overnight. The reaction was cooled in an ice bath and quenched with a 20% solution of ammonium chloride (3 L). The organic layer was removed and the aqueous layer extracted with ethyl acetate. The organic layers were combined, washed with saturated salt solution, and dried over anhydrous magnesium sulfate. The solution was filtered through a pad of anhydrous sodium sulfate and the solvent removed by rotoevaporation to yield the title compound (265.7 gm, 92.3% yield).

20-tert-Butyldimethylsilyloxy-7-methyl-pregn-4,6-diene-3-one

A solution of 20-tert-butyldimethylsilyloxy-7-methyl-pregn-5-ene-3,7-diol (298 gm, 0.59 mol) in toluene (3 L) and cyclohexanone (1.03 L) was azeotroped to remove 750 mL of solvent. A solution of aluminum isopropoxide (121 gm) in toluene (620 mL) was added and the solution azeotroped to remove another 650 mL of solvent. A reflux condenser was added and the solution refluxed overnight. The solution was cooled to 40° C. and Supercell® (125 gm) and water (125 mL) were added. After stirring for 10 min, the mixture was filtered and the solids washed with toluene (550 mL). The solvent was removed by rotoevaporation to yield a orange liquid which was purified by column chromatography on silica gel eluted with hexane, followed by 5–10% ethyl acetate in hexanes. The title compound was isolated as a mixture of 20α- and 20β-isomers (199.4 gm, 76% yield).

20-tert-Butyldimethylsilyloxy-7β-methyl-pregn-4-ene-3-one

A slurry of 5% palladium on carbon (7.12 gm) and benzyl alcohol (213 mL) in heptane (356 mL) was refluxed for 20 min. The mixture was cooled to 80° C. and a solution of 20-tert-butyldimethylsilyloxy-7-methyl-pregn-4,6-diene-3-one (71.2 gm, 0.16 mol) in heptane (427 mL) was added. The slurry was refluxed for 9.5 hr. The reaction was cooled to room temperature and filtered through solka flok filter aid which was subsequently washed with hexane. The filtrate was extracted with acetonitrile which was subsequently back extracted with hexane. The heptane and hexane extracts were combined, washed with saturated sodium sulfate and saturated salt solutions, and dried over anhydrous magnesium sulfate. The solution was filtered through a pad of anhydrous sodium sulfate and the solvent removed by rotoevaporation. The title compound was purified by column chromatography on silica gel eluted with 7% ethyl acetate in hexanes (31.4 gm, 44% yield).

20-tert-Butyldimethylsilyloxy-7β-methyl-5-oxo-A-nor-3,5-secopregnan-3-oic acid

To a solution of 20-tert-butyldimethylsilyloxy-7β-methyl-pregn-4-ene-3-one (73.57 gm, 0.165 mol) in tert-butanol (0.96 L) was added a solution of sodium carbonate (25.8 gm) in water (120 mL). The mixture was heated to 80° C. with stirring. A warm solution of sodium periodate (244 gm) and potassium permanganate (1.91 gm) in water (0.96 L) was slowly added and then the reaction refluxed for 2 hr. The reaction was cooled to room temperature and filtered through a pad of SuperCell. The filter cake was washed with water (2×190 mL). The combined filtrates were rotoevaporated to remove the tert-butanol and washed with methylene chloride. The aqueous solution was acidified to pH ~3 with 2N hydrochloric acid and extracted with methylene chloride (3×). The organic extracts were combined, washed with 5% sodium bisulfite solution and saturated salt solution, and dried over anhydrous magnesium sulfate. The solvent was removed by rotoevaporation to yield the title compound as a white foam (62.3 gm, 83% yield).

20-tert-Butyldimethylsilyloxy-7β-methyl-4-azapregn-5-ene

To a solution of 20-tert-butyldimethylsilyloxy-7β-methyl-5-oxo-A-nor-3,5-secopregnan-3-oic acid (26 gm., 56 mmol) in ethylene glycol (500 mL) under nitrogen was added anhydrous ammonium acetate (50 gm). The mixture was heated at 180° C. for 5 hr, cooled to room temperature, and diluted with water (3.5 L). After stirring for 1 hr, the solid was filtered and the aqueous layer was extracted with methylene chloride (500 mL). The organic layer was dried over anhydrous magnesium sulfate and the solvent removed by rotoevaporation. The residue was combined with the filtered solid and dried in a vacuum oven overnight to give the title compound (23.9 gms, 96% yield).

20-tert-Butyldimethylsilyloxy-7β-methyl-5α-4-azapregnane

To a solution of 20-tert-butyldimethylsilyloxy-7β-methyl-4-azapregn-5-ene (23.9 gms, 53.6 mmol) in acetic acid (250 mL) was added platinum oxide (1.8 gm). The mixture was stirred overnight under hydrogen (1 atmosphere). The reaction mixture was filtered through a pad of celite filter aid and the filtrate was coevaporated with toluene (3×500 mL) to remove all of the acetic acid. The residue was dissolved in chloroform and filtered again through a pad of celite filter aid to remove residual catalyst. The solvent was removed by rotoevaporation to yield the title compound which was taken directly on to the next step without any further purification.

20-Hydroxy-7β-methyl-5α-4-azapregnane-3-one

To a slurry of crude 20-tert-butyldimethylsilyloxy-7β-methyl-5α-4-azapregnane (25.2 gms) in acetonitrile (300 mL) was added an aqueous solution of hydrofluoric acid (12 mL). After stirring for 8 hr at room temperature, the reaction mixture was cooled to 0° C. and saturated sodium bicarbonate solution was slowly added. The mixture was extracted with methylene chloride (3×500 mL) and the combined extracts washed with water, saturated salt solution and dried over anhydrous sodium sulfate. The solvent was removed by rotoevaporation to give the title compound (22.3 gms) which was used without purification in the subsequent reaction.

7β-Methyl-5α-4-azapregnane-3,20-dione

To a stirred solution of 20-hydroxy-7β-methyl-5α-4-azapregnane-3-one (22.3 gms, 67 mmol) in dry methylene chloride under nitrogen (110 mL) was added 4-methyl morpholine N-oxide (11.8 gms, 100 mmol) followed by 4 Å molecular sieves (33 gm). To this mixture was added tetrapropylammonium perruthenate (1.2 gm). After stirring at room temperature for 4 hr, the reaction mixture was poured through pad of silica gel in a 300 mL sintered glass funnel which was subsequently eluted with 4:1 ethyl acetate/methylene chloride (5 L). The solvent was removed by rotoevaporation and the title compound recrystallized (16.3 gm).

7β-Methyl-5α-4-azapregn-1-ene-3,20-dione

To a solution of 7β-methyl-5α-4-azapregnane-3,20-dione (5.5 gm, 16.6 mmol) in dry toulene (100 mL) was added 2,3-dichloro-5,6-dicyano-1,4-benzoquinone (DDQ, 4.52 gm, 19.92 mmol) followed by bis(trimethylsilyl) trifluoroacetamide (17.6 mL, 66.4 mmol) and triflic acid (0.11 mL, 1.3 mmol). The mixture was stirred under nitrogen for 24 hr at room temperature after which methyl acetoacetate (1.8 mL, 1.66 mmol) was added and stirring continued for 4 hr followed refluxing for 48 hr. The reaction mixture was poured into water (500 mL) containing sodium bicarbonate (8 gm) and sodium sulfite (3 gm). The solution was extracted with methylene chloride (3×250 mL), washed with water, saturated salt solution, and dried over anhydrous sodium sulfate. The solvent was removed by rotoevaporation and the product purified by flash column chromatography on silica gel eluted with 10% isopropanol in hexane as eluent to the title compound (2.47 gm).

EXAMPLE 2

4,7β,20-Trimethyl-20-hydroxy-5α-4-azapregnan-3-one

To a solution of 103 mg (0.31 mmol) 7β-methyl-5α-4-azapregnan-3,20-dione in 10 ml dry tetrahydrofuran at –40° C. under $N_2$ was added 6 eq methylmagnesium bromide (1.86 mmol) in ether. The reaction was stirred and allowed to warm to RT over 90 minutes. Aqueous ammonium chloride (5 ml) was added and the solvents were evaporated. The residue was partitioned between methylene chloride and water. The organic layer was washed with brine, dried over magnesium sulfate, and evaporated. The crude residue was dissolved in 5 ml dry dimethylformamide and cooled to 0° C. Methyl iodide (10 eq, 3.1 mmol) and sodium hydride (2 eq, 0.6 mmol) were added and the reaction was stirred at RT for 48 hours. Aqueous ammonium chloride was added and the reaction mixture was poured onto 100 ml water and extracted with three 25 ml portions of ethyl acetate. The organic layer was washed with water, brine, dried over magnesium sulfate, and evaporated. The product was purified via HPLC on a 19×300 mm 8 micron silica column using a 5 to 20% isopropanol/hexane gradient at 20 ml/min to yield 51 mg (0.141 mmol, 46% yield) of the title compound.

MS (FAB): M+1=362

NMR (CDCl$_3$, δ from TMS): 0.82 (s, 3H), 0.83 (s, 3H), 1.03 (d, J=6.14 Hz, 3H), 1.17 (s, 3H), 1.28 (s, 3H), 2.42 (m, 2H), 2.90 (s, 3H), 3.03 (m, 1H).

EXAMPLE 3

7β,20-dimethyl-20-hydroxy-5α-4-azapregn-1-en-3-one

To a solution of 20 mg (0.06 mmol) 7β-methyl-5α-4-azapregn-1-ene-3,20-dione in 4 ml dry tetrahydrofuran at –40° C. under $N_2$ was added 10 eq methylmagnesium bromide (0.6 mmol) in ether. The reaction was stirred and allowed to warm to RT over 18 hours. Aqueous ammonium chloride (5 ml) was added and the solvents were evaporated. The residue was partitioned between methylene chloride and water. The organic layer was washed with brine, dried over magnesium sulfate, and evaporated. The product was purified via HPLC on a 19×300 mm 8 micron silica column using 5% isopropanol/hexane at 20 ml/min to yield 16 mg (0.046 mmol, 77% yield) of the title compound.

MS(EI): M+=345, M(—CH3)=330, M(—CH$_3$,H$_2$O)=312

NMR (CDCl$_3$, δ from TMS): 0.84 (s, 3H), 0.89 (s, 3H), 1.01 (d, J=5.8 Hz, 3H), 1.17 (s, 3H), 1.29 (s, 3H), 2.42 (m, 2H), 3.3 (m, 1H), 5.22 (b, 1H), 5.79 (dd, Ja=2.4 Hz, Jb=9.9 Hz, 1H), 6.78 (d, J=9.9 Hz).

EXAMPLE 4

4,7β,20-trimethyl-20-hydroxy-5α-4-azapregn-1-en-3-one

To a solution of 73 mg (0.22 mmol) 7β-methyl-5α-4-azapregn-1-ene-3,20-dione in 7 ml dry tetrahydrofuran at –40° C. under $N_2$ was added 3 eq methyllithium (0.7 mmol) in ether. The reaction was stirred and monitored by TLC. After three hours a second (0.5 eq) portion of methyllithium was added. After two hours 10 eq methyl iodide (2.2 mmol) was added and the reaction was allowed to warm to room temperature over 18 hrs. Aqueous ammonium chloride (5 ml) was added and the solvents were evaporated. The residue was partitioned between ethyl acetate and water. The organic layer was washed with brine, dried over magnesium sulfate, and evaporated. The product was purified via HPLC on a 19×300 mm 8 micron silica column using a 5 to 15% isopropanol/hexane gradient at 20 ml/min to yield 34 mg (0.095 mmol, 43% yield) of the title compound.

MS(EI): M+=359

NMR (CDCl$_3$, δ from TMS): 0.84 (s, 6H), 1.05 (d, J=5.9 Hz, 3H), 1.17 (s, 3H), 1.29 (s, 3H), 2.4 (m, 2H), 2.93 (s, 3H), 3.3 (m, 1H), 5.83 (d, J=9.9 Hz, 1H), 6.67 (d, J=9.9 Hz, 1H).

EXAMPLE 5

4,7β-dimethyl-20-ethyl-20(S)-hydroxy-5α-4-azapregnan-3-one

To a solution of 90 mg (0.27 mmol) 7β-methyl-5α-4-azapregnan-3,20-dione in 10 ml dry tetrahydrofuran at –40° C. under $N_2$ was added 10 eq ethylmagnesium bromide (2.7 mmol) in ether. The reaction was stirred and allowed to warm to RT over 90 minutes. Aqueous ammonium chloride (5 ml) was added and the solvents were evaporated. The residue was partitioned between methylene chloride and water. The organic layer was washed with brine, dried over magnesium sulfate, and evaporated. The crude residue was purified via HPLC on a 19×300 mm 8 micron silica column using a 5 to 10% isopropanol/hexane gradient at 20 ml/min to yield 65 mg (0.18 mmol, 65%) of the 4NH azasteroid. A solution of 63 mg (0.17 mmol) in 5 ml dry dimethylformamide was cooled to 0° C. under $N_2$. Methyl iodide (10 eq, 1.7 mmol) and sodium hydride (1.2 eq, 0.2 mmol) were added and the reaction was stirred at RT for 24 hours at RT. Aqueous ammonium chloride was added and the reaction mixture was poured onto 100 ml water and extracted with three 25 ml portions of ethyl acetate. The organic layer was washed with water, brine, dried over magnesium sulfate, and evaporated. The product was purified via HPLC on a 19×300 mm 8 micron silica column using a 5 to 10% isopropanol/hexane gradient at 20 ml/min to yield 40 mg (0.106 mmol, 63% yield) of the title compound.

MS (EI): M+=375

NMR (CDCl$_3$, δ from TMS): 0.82 (s, 3H), 0.82 (t, J=7.5 Hz, 3H), 0.85 (s, 3H), 1.03 (d, J=6.1 Hz, 3H), 1.23 (s, 3H), 2.42 (m, 2H), 2.90 (s, 3H), 3.0 (m, 1H).

EXAMPLE 6

7β-methyl-20-ethyl-20(S)-hydroxy-5α-4-azapregn-1-en-3-one

To a solution of 100 mg (0.303 mmol) 7β-methyl-5α-4-azapregn-1-ene-3,20-dione in 10 ml dry tetrahydrofuran at –40° C. under $N_2$ was added 15 eq ethylmagnesium bromide (4.5 mmol) in ether. The reaction was stirred and allowed to warm to RT over 18 hours. Aqueous ammonium chloride (5 ml) was added and the solvents were evaporated. The residue was partitioned between methylene chloride and water. The organic layer was washed with brine, dried over magnesium sulfate, and evaporated. The product was purified via HPLC on a 19×300 mm 8 micron silica column using 5% isopropanol/hexane at 20 ml/min to yield 53 mg (0.147 mmol, 49% yield) of the title compound.

MS(FAB): M+=360

NMR (CDCl$_3$, δ from TMS): 0.83 (t, J=7.5 Hz, 3H), 0.87 (s, 3H), 0.89 (s, 3H), 1.02 (d, J=5.7 Hz, 3H), 1.23 (s, 3H), 3.32 (m, 1H), 5.79 (dd, Ja=2.4 Hz, Jb=9.9 Hz, 1H), 6.79 (d, J=10.0 Hz).

EXAMPLE 7

4,7β-dimethyl-20-ethyl-20(S)-hydroxy-5α-4-azapregn-1-en-3-one

A solution of 46 mg (0.128 mmol) of 7β-methyl-20-ethyl-20(S)-hydroxy-5α-4-azapregn-1-en-3-one (from Example 6) in 5 ml dry dimethylformamide was cooled to 0° C. under N$_2$. Methyl iodide (10 eq, 1.3 mmol) and sodium hydride (2 eq, 25 mmol) were added and the reaction was stirred at RT for 24 hours. Aqueous ammonium chloride was added and the reaction mixture was poured onto 100 ml water and extracted with three 25 ml portions of ethyl acetate. The organic layer was washed with water, brine, dried over magnesium sulfate, and evaporated. The product was purified by silica gel MPLC using 10% acetone/methylene chloride to yield 30 mg (0.08 mmol, 63% yield) of the title compound.

MS (FAB): M+=374

NMR (CDCl$_3$, δ from TMS): 0.82 (t, J=7.5 Hz, 3H), 0.85 (s, 3H), 0.87 (s, 3H), 1.02 (d, J=5.7 Hz, 3H), 1.23 (s, 3H), 2.93 (s, 3H), 3.32 (m, 1H), 5.83 (d, Jb=10.0 Hz, 1H), 6.68 (d, J=10.0 Hz).

EXAMPLE 8

20-methoxy-4,7β,20-trimethyl-5α-4-azapregnan-3-one

To a solution of 20 mg (0.06 mmol) 20-hydroxy-4,7β,20-trimethyl-5α-4-azapregnan-3-one (from Example 2) in 4 ml dry dimethylformamide at 0° C. was added methyl iodide (10 eq, 0.6 mmol) and sodium hydride (5 eq, 0.3 mmol) were added and the reaction was stirred at RT for 48 hours. Aqueous ammonium chloride was added and the reaction mixture was poured onto 100 ml water and extracted with three 25 ml portions of ethyl acetate. The organic layer was washed with water, brine, dried over magnesium sulfate, and evaporated. The product was purified via HPLC on a 19×300 mm 8 micron silica column using 5% isopropanol/hexane eluent at 20 ml/min to yield 15 mg (0.04 mmol, 67% yield) of the title compound.

MS (EI): M+=375, M—CH$_3$=360

NMR (CDCl$_3$, δ from TMS): 0.77 (s, 3H), 0.82 (s, 3H), 1.02 (d, J=6.1 Hz, 3H), 1.16 (s, 3H), 1.16 (s, 3H), 2.42 (m, 2H), 2.90 (s, 3H), 3.0 (m, 1H), 3.13 (s, 3H).

Biological Assays

Preparation of Human prostatic and scalp 5α-reductases

Samples of human tissue were pulverized using a freezer mill and homogenized in 40 mM potassium phosphate, pH 6.5, 5 mM magnesium sulfate, 25 mM potassium chloride, 1 mM phenylmethylsulfonyl fluoride, 1 mM dithiothreitol (DTT) containing 0.25M sucrose using a Potter-Elvehjem homogenizer. A crude nuclear pellet was prepared by centrifugation of the homogenate at 1,500× g for 15 min. The crude nuclear pellet was washed two times and resuspended in two volumes of buffer. Glycerol was added to the resuspended pellet to a final concentration of 20%. The enzyme suspension was frozen in aliquots at =80° C. The prostatic and scalp reductases were stable for at least 4 months when stored under these conditions.

5α-reductase assay

The reaction mixture contained in a final volume of 100 μl is: 40 mM buffer (human scalp, potassium phosphate, pH 6.5; human prostatic 5α-reductase, sodium citrate, pH 5.5), 0.3–10 μM $^{14}$C-T (or $^3$H-T), 1 mM DTT, and 500 μM NADPH. Typically, the assay was initiated by the addition of 50–100 μg prostatic homogenate or 75–200 μg scalp homogenate and incubated at 37° C. After 10–50 min the reaction was quenched by extraction with 250 μl of a mixture of 70% cyclohexane: 30% ethyl acetate containing 10 μg each DHT and T. The aqueous and organic layers were separated by centrifugation at 14,000 rpm in an Eppendorf microfuge. The organic layer was subjected to normal phase HPLC (10 Whatman partisil 5 silica column equilibrated in 1 ml/min 70% cyclohexane: 30% ethyl acetate; retention times DHT, 6.8–7.2 min; androstanediol, 7.6–8.0; T, 9.1–9.7 min). The HPLC system consisted of a Waters Model 680 Gradient System equipped with a Hitachi Model 655A autosampler, Applied Biosystems Model 757 variable UV detector, and a Radiomatic Model A120 radioactivity analyzer. The conversion of T to DHT was monitored using the radioactivity flow detector by mixing the HPLC effluent with one volume of Flo Scint 1 (Radiomatic). Under the conditions described, the production of DHT was linear for at least 25 min. The only steroids observed with the human prostate and scalp preparations were T, DHT and androstanediol.

Inhibition studies

Compounds were dissolved in 100% ethanol. The compound to be tested was pre-incubated with the enzyme (either 5α-reductase type 1 or 2) prior to initiation by addition of substrate testosterone. IC$_{50}$ values represent the concentration of inhibitor required to decrease enzyme conversion of testosterone to dihydrotestosterone by 50% of the control. IC$_{50}$ values were determined using a 6 point titration where the concentration of the inhibitor was varied from 0.1 to 1000 nM. Representative compounds of this invention were tested in the above described assay for 5α-reductase type 1 and type 2 inhibition.

A compound referred to herein as a 5α-reductase 2 inhibitor is a compound that shows inhibition of the 5α-reductase 2 isozyme in the above-described assay, having an IC$_{50}$ value of about or under 100 nM.

Human Dermal Papilla Cell Assay

The dermal papilla is a small group of cells at the base of each hair follicle, and it is presently thought that these cells are stem cells that form the basis for hair growth. These cells have been shown to have 5 alpha reductase activity, and it is therefore possible to test inhibitors of 5 alpha reductase in these cell culture systems.

Isolated and cultured dermal papilla cells are prepared according to the methods of Messenger, A. G., *The Culture of Dermal Papilla Cells From Human Hair Follicles*, Br. J. Dermatol. 110:685–689, 1984 and Itami, S. et. al., *5α-Reductase Activity In Cultured Human Dermal Papilla Cells From Beard Compared With Reticular Dermal Fibroblasts*, J. Invest. Dermatol. 94:150–152, 1990. Beard dermal papilla cells and occipital scalp hair of two different individuals are used throughout the study. All experiments are performed at confluency after the fourth to sixth subculture. Confluent monolayers are rinsed twice with phosphate-buffered saline, scraped from dishes by rubber policemen, and collected into a centrifuge tube. The cell suspensions are centrifuged at 1,500 rpm for 10 min at 4° C. The pellets are resuspended in 20 mM Tris-HCl buffer, pH 7.5, at 4° C., containing 250 mM sucrose, 1 mM MgCl$_2$, and 2 mM CaCl$_2$, by vortexing and 10 passes through a 25-gauge needle. The crude homogenate is further homogenized by a teflon-glass homogenizer, and is used as the cell homogenate. For the study of subcellular localization of 5α-reductase, the cell homogenate is centrifuged at 800× g for 10 min to yield a crude nuclear pellet. The resultant supernatant is centrifuged at 10,000× g for 15 min to produce a crude mitochondrial pellet. The supernatant is centrifuged at 100,000× g for 60 min to yield a microsomal pellet and cytosol. Each particulate fraction is washed twice and resuspended in the buffer.

A standard incubation mixture will consist of 50 nM [$^3$H]-testosterone, 1 mM NADPH, 100 mM sodium citrate, pH 5.5 or 100 mM Tris-HCl, pH 7.5, and 50 μl of the cell homogenate, in a final volume of 100 μl. Each tube contains 50–100 μg of cellular protein. Incubation is carried out at 37° C. for 30 min. During this incubation, the reaction is proportional to the time. For the study of optimum pH, citrate buffer is used at pH 4.5–6.5, and the Tris HCl buffer at pH 7.0–9.0. The protein content is determined by the method of Lowry, et. al., *Protein Measurement With The Folin Phenol Reagent*, J. Biol. Chem. 193:265–275, 1951.

After incubation, the reaction is stopped by adding 4 times volume of chloroform-methanol (2/1:V/V) containing 110 μg each of carrier steroids. The extracted steroids are analyzed by thin-layer chromatographyl as previously described by Gomez, et. al., *In Vitro Metabloism Of Testosterone-4-$^{14}C$ and $\Delta$-androstene-3, 17-dione-4-$^{14}C$ In Human Skin*, Biochem. 7:24–32, 1968, and the purity of each steroid is determined by the recrystallization method. The activity of 5α-reductase is expressed by the sum of dihydrotestosterone, androstanediol and androstanedione formed. [1,2-$^3$H]-testosterone (55.2 Ci/mmol) is obtainable from New England Nuclear Corporation (Boston, Mass.) and unlabeled steroids can be purchased from Sigma Chemical Company (St. Louis, Mo.). Fetal calf serum is obtainable from Hazleton (Lenaxa, Kans.). All other chemicals are of reagent grade.

Fuzzy Rat Acne Model

Adult fuzzy rats are a variety of rat that has stunted hair growth, brown colored seborrhea coveting their entire back skin and abnormally increased sebum production after puberty that has been demonstrataed to be due to circulating androgens. 0.1, 0.05 and 0.025% solutions of a selected 5α-reductase inhibitor of interest are prepared in a vehicle of propylene glycol, isopropanol, isopropyl myristate and water (50/30/2/18%), and is topically applied onto the backs of adult male fuzzy rats, 0.2 ml per animal daily for 4 weeks. Controls receive the vehicle alone and 5 of them are castrated. After 2 weeks seborrhea will be dose-dependently depleted and after 4 weeks bromodeoxyuridine (BrdU, 200 mg/kg) is intraperitoneally injected 2 hours before sacrifice. The skin tissues are incubated with EDTA (20 mM) in phosphate buffer, 1.5 hours at 37° C. The pilo-sebaceous unit attached to the epidermis is striped from the dermis and fixed with formalin for immuno-staining of BrdU. DNA synthesis cells showing a BrdU-positive nucleus are located in the outer glandular border. The number of S-phase cells per lobe is determined with a micro-image apparatus. Using formalin fixed skin, frozen serial sections are stained with 1% osmium and the size of the lobes is measured. A positive inhibitor of skin 5α-reductrase will induce suppression of sebum production by inhibiting the rate of glandular cell turnover, and showing reduced lobular size.

The present invention has the objective of providing suitable topical, oral and parenteral pharmaceutical formulations for use in the novel methods of treatment of the present invention.

The compositions containing the compounds of the present invention as the active ingredient for use in the treatment of e.g., benign prostatic hypertrophy, prostatitis, and treatment [and prevention] of prostatic carcinoma, hyperandrogenic conditions, can be administered in a wide variety of therapeutic dosage forms in conventional vehicles for systemic administration, as, for example, by oral administration in the form of tablets, capsules, solutions, or suspensions, or by injection. The daily dosage of the products may be varied over a wide range varying from 0.5 to 1,000 mg per adult human/per day. The compositions are preferably provided in the form of scored tablets containing 0.5, 1.0, 2.5, 5.0, 10.0, 15.0, 25.0, and 50.0 milligrams of the active ingredient for the symptomatic adjustment of the dosage to the patient to be treated. An effective amount of the drug is ordinarily supplied at a dosage level of from about 0.002 mg to about 50 mg/kg of body weight per day. Preferably the range is from about 0.01 mg to 7 mg/kgs of body weight per day. These dosages are well below the toxic dose of the product. For the treatment of androgenic alopecia, acne vulgaris, seborrhea, female hirsutism, the compounds of the present invention are administered in a pharmaceutical composition comprising the active compound in combination with a pharmacologically acceptable carrier adapted for topical, oral or parenteral administration.

These topical pharmaceutical compositions may be in the form of a cream, ointment, gel or aerosol formulation adapted for application to the skin. These topical pharmaceutical compositions containing the compounds of the present invention ordinarily include about 0.1% to 15%, preferably about 5%, of the active compound, in admixture with about 95% of vehicle.

The compounds of the present invention can be administered in such oral dosage forms as tablets, capsules (each including timed release and sustained release formulations), pills, powders, granules, elixers, tinctures, suspensions, syrups and emulsions. Likewise, they may also be administered in intravenous (both bolus and infusion), intraperitoneal, subcutaneous or intramuscular form, all using forms well known to those of ordinary skill in the pharmaceutical arts. An effective but non-toxic amount of the compound desired can be employed as a 5α-reductase agent.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. An ordinarily skilled physician or veterinarian can readily determine and prescribe the effective amount of the drug required to prevent, counter or arrest the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug.

Oral dosages of the present invention, when used for the indicated effects, will range from about 0.01 mg to 50 mg/kgs of body weight per day. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittant throughout the dosage regimen.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drag component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, zanthan gum and the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropyl-methacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

While the invention has been described and illustrated with reference to certain preferred embodiments thereof, those skilled in the art will appreciate that various changes, modifications and substitutions can be made therein without departing from the spirit and scope of the invention. For example, effective dosages other than the preferred dosages as set forth herein above may be applicable as a consequence of variations in the responsiveness of the mammal being treated for any of the indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be limited only by the scope of the claims which follow and that such claims be interpreted as broadly as is reasonable.

What is claimed is:

1. A compound of the formula I

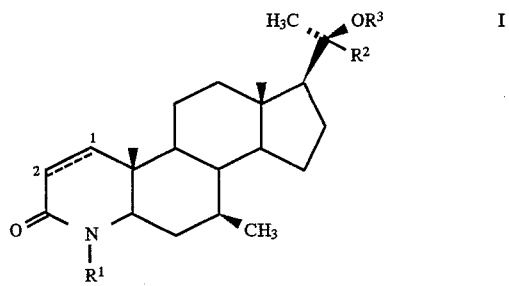

wherein:

$R^1$ is selected from the group consisting of hydrogen and methyl;

$R^2$ is selected from the group consisting of methyl and ethyl;

$R^3$ is selected from the group consisting of hydrogen and methyl; and the C1–C2 carbon-carbon bond may be a single bond or a double bond.

2. A compound selected from the group:

4,7β,20-trimethyl-20-hydroxy-5α-4-azapregnan-3-one;

7β,20-dimethyl-20-hydroxy-5α-4-azapregn-1-en-3-one;

4,7β,20-trimethyl-20-hydroxy-5α-4-azapregn-1-en-3-one;

4,7β-dimethyl-20-ethyl-20(S)-hydroxy-5α-4-azapregnan-3-one;

7β-methyl-20-ethyl-20(S)-hydroxy-5α-4-azapregn-1-en-3-one;

4,7β-dimethyl-20-ethyl-20(S)-hydroxy-5α-4-azapregn-1-en-3-one; and 20-methoxy-4,7β,20-trimethyl-5α-4-azapregnan-3-one.

3. A method for treating, in a human in need thereof, the hyperandrogenic condition of acne administering to said human 0.5 to 1000 mg/day of the compound as claimed in claim 1 alone or in combination with.

4. The method as claimed in claim 3, wherein said inhibitor of 5α-reductase 2 is finasteride.

5. A pharmaceutical composition comprising a pharmaceutically acceptable carrier and a 0.5 to 1000 mg of a compound as claimed in claim 1.

* * * * *